United States Patent [19]

Heldebrandt et al.

[11] Patent Number: 5,262,442
[45] Date of Patent: Nov. 16, 1993

[54] PROCESS FOR RAPID THAWING AND STORAGE OF FROZEN FLUOROCARBON EMULSION, AND RESULTANT PRODUCT

[75] Inventors: Charles M. Heldebrandt, Arcadia; Charles H. Davis, Jr., Westminster, both of Calif.

[73] Assignee: Alpha Therapeutic Corporation, Los Angeles, Calif.

[21] Appl. No.: 812,937

[22] Filed: Dec. 24, 1991

[51] Int. Cl.⁵ .............................. A61K 47/00
[52] U.S. Cl. ................... 514/772; 514/832; 514/833; 514/937
[58] Field of Search ............ 424/5; 514/759, 832, 514/937, 772, 833

[56] References Cited

U.S. PATENT DOCUMENTS

| | | | |
|---|---|---|---|
| 3,823,091 | 7/1974 | Samejima et al. | 514/832 |
| 4,252,827 | 2/1981 | Yokoyama et al. | 514/759 |
| 4,461,717 | 7/1984 | Moore | 514/832 |
| 4,942,179 | 7/1990 | Borgarello | 514/832 |
| 5,077,036 | 12/1991 | Long, Jr. | 514/759 |

Primary Examiner—Frederick E. Waddell
Assistant Examiner—Raymond J. Henley, III
Attorney, Agent, or Firm—Sughrue, Mion, Zinn, Macpeak & Seas

[57] ABSTRACT

A method for rapidly preparing a frozen fluorocarbon emulsion for administration without degradation and having an extended shelf life is disclosed.

8 Claims, No Drawings

PROCESS FOR RAPID THAWING AND STORAGE OF FROZEN FLUOROCARBON EMULSION, AND RESULTANT PRODUCT

FIELD OF THE INVENTION

The invention relates to a method of rapidly preparing a frozen oxygen-transporting fluorocarbon emulsion for administration, the emulsion after thawing being stable for extended periods of time.

BACKGROUND OF THE INVENTION

Fluorocarbon emulsions are known as a substitute fluid capable of transporting oxygen with various beneficial uses such as serving as an artificial blood substitute and as a perfusion fluid. Recently, fluorocarbon emulsions have been used during percutaneous transluminal coronary angioplasty and in the treatment of myocardial infarction.

Suitable stable emulsions in a physiologically acceptable aqueous medium comprise at least one oxygen-transferable perfluorocarbon compound having 9-11 carbon atoms, at least one perfluorotert-amine, a high molecular weight nonionic surfactant, a phospholipid and a fatty acid, with a particle size of about 0.05 $\mu$m to about 0.3 $\mu$m.

Generally, emulsions of the aforementioned type are stored frozen. The emulsion is thawed in a water bath held at about 37.5° C., which takes about 45 minutes, is mixed with various buffers, stabilizers and osmotically active compounds to render the emulsion physiologic and then can be oxygenated prior to administration.

It is believed that the emulsions are labile and sensitive, preventing their thawing at temperatures above 37.5° C. without degradation, and requiring that upon thawing administration within eight hours. At present, any emulsion that is thawed and not used within eight hours of thawing, as a common practice, is discarded.

Accordingly, it would be beneficial if the frozen perfluorochemical emulsions could be thawed rapidly and could be maintained at room temperature or at refrigerator temperatures for a longer period of time following thawing. Then, the emulsions would be available for immediate use in life-threatening medical emergencies such as in coronary angioplasty and in conjunction with the administration of fibrinolytic agents in treating myocardial infarction.

SUMMARY OF THE INVENTION

It is an object of the invention to provide a method for rapidly thawing a frozen oxygen-transporting fluorocarbon emulsion for administration without degradation of the emulsion.

Another object of the present invention is to provide a method for rapidly thawing a frozen fluorocarbon emulsion which can be stored in the thawed state for over 8 hours.

The above and other objects were achieved in the development of a method of rapid thawing of the frozen emulsion at temperatures ranging from about 40° C. to about 100° C. resulting in a liquid emulsion that can be stored in a refrigerator or at ambient temperature for up to fifteen days, depending on the thaw temperature.

DETAILED DESCRIPTION OF THE INVENTION

According to the invention, there is provided a stable emulsion of an oxygen-transporating perfluorocarbon compound having a particle size of about 0.05 $\mu$m to about 0.3 $\mu$m, which comprises at least one perfluorocarbon compound having 9 to 11 carbon atoms selected from perfluorodecalin, perfluoromethyldecalin, perfluoroalkylcyclohexanes having 3 to 5 carbon atoms in the alkyl, perfluoroalkyltetrahydrofurans having 5 to 7 carbon atoms in the alkyl, perfluoroalkyltetrahydropyrans having 4 to 6 carbon atoms in the alkyl or perfluoroalkanes having 9 to 11 carbon atoms; at least one perfluorotert-amine having 9 to 11 carbon atoms selected from perfluorotert-alkylamines having 9 to 11 carbon atoms, perfluoro-N-alkylpiperidines having 4 to 6 carbon atoms in the alkyl or perfluoro-N-alkylmorpholines having 5 to 7 carbon atoms in the alkyl; a high molecular weight nonionic surfactant having a molecular weight of about 2,000 to about 20,000; a phospholipid; and at least one fatty acid compound selected from fatty acids having 8 to 22 carbon atoms, physiologically acceptable salts thereof or monoglycerides thereof; wherein the ratio of said perfluorocarbon compound to said perfluorotert-amine is 95-50 : 5-50 by weight.

The high molecular weight nonionic surfactant has a molecular weight of about 2,000 to about 20,000 and includes polyoxyethylene-polyoxypropylene copolymers, polyoxyethylene alkyl ethers and polyoxyethylene alkylaryl ethers. The concentration of said surfactant in the emulsion is about 2.0% to about 5.0%, preferably from about 3.0% to about 3.5%. (Unless indicated otherwise, all percentages refer to the amount proportion of a material by weight (e.g., grams) based on 100 ml of the resulting emulsion.)

Examples of perfluorocarbons having 9 to 11 carbon atoms are perfluorocycloalkanes or perfluoroalkylcycloalkanes which include, for example, perfluoro-$C_{3-5}$-alkylcyclohexanes such as perfluoromethylpropylcyclohexane, perfluorobutylcyclohexane, perfluorotrimethylcyclohexane, perfluoroethylpropylcyclohexane, perfluorodecalin and perfluoromethyldecalin; perfluoro-$C_{4-6}$-alkyltetrahydropyrans such as perfluorohexyltetrahydropyran; perfluoro-$C_{5-7}$-alkyltetrahydrofurans such as perfluoropentyltetrahydrofuran, perfluorohexyltetrahydrofuran and perfluoroheptyltetrahydrofuran; and perfluoroalkanes having 9–11 carbon atoms such as perfluorononane and perfluorodecane. Perfluorodecalin is preferred.

Examples of the perfluorotert-amine having 9 to 11 carbon atoms are perfluorotert-alkylamines having 9 to 11 carbon atoms which include, for example, perfluorotrialkylamines such as perfluoroN,N-dibutylmonomethylamine, perfluoro-N,N-diethylpentylamine, perfluoro-N,N-diethylhexylamine, perfluoro-N,N-dipropylbutylamine and perfluorotripropylamine; perfluoro-N,N-dialkylcyclohexylamines having 9–11 carbon atoms such as perfluoro-N,N-diethylcyclohexylamine; perfluoro-N-$C_{4-6}$-alkylpiperidines such as perfluoro-N-pentyl-piperidine, perfluoro-N-hexylpiperidine and perfluoro-N-butylpiperidine; and perfluoroN-$C_{5-7}$-alkylmorpholines such as perfluoro-N-pentylmorpholine, perfluoro-N-hexylmorpholine and perfluoro-N-heptylmorpholine. Perfluorotripropylamine is preferred.

The ratio of the perfluorocarbon compound to the perfluorotert-amine is 50–95 : 50–5 by weight and the total amount of perfluorocarbon compound and perfluorotert-amine in the emulsion is about 10% to about 50%.

The phospholipids can be those comprising egg yolk phospholipid or soybean phospholipid with egg yolk phospholipids preferred. The amount used in the emulsion ranges from about 0.1% to about 1.0%, and preferably about 0.4% to about 0.6%.

The fatty acid compound is a fatty acid having 8 to 22 carbon atoms, a physiologically acceptable salt such as the sodium or potassium salt thereof or a monoglyceride thereof, which includes, for example, caprylic acid, capric acid, lauric acid, myristic acid, palmitic acid, stearic acid, behenic acid, palmitoleic acid, oleic acid, linoleic acid and arachidonic acid, the sodium or potassium salt thereof and a monoglyceride thereof. Preferable fatty acid compounds are those having 14 to 20 carbon atoms, and their physiologically acceptable salts, and the most preferable are potassium palmitate and potassium oleate. The fatty acid compounds may be used alone or as a mixture in an amount of about 0.004% to about 0.1%, and preferably about 0.02% to about 0.04%.

The fluorocarbon compound emulsion of the invention is prepared by adding prescribed amounts of the above-mentioned components, in any order, to a physiologically acceptable aqueous medium, such as distilled water, agitating the mixture to obtain a crude emulsion and then emulsifying the crude emulsion by means of an effective emulsifier until the average particle diameter becomes about 0.05 $\mu$m to about 0.3 $\mu$m.

The emulsification is attained, for example, by means of a high pressure homogenizer, which is a high pressure pump that homogenizes a mixture of two immiscible liquids by injection through a slit under high pressure at high velocity to give shear thereby mixing the liquids. A typical homogenizer is one which has multiple-stage valves each having a spring therein by which slits are formed.

When using such a homogenizer with multiple-stage valves, the mixture is circulated several times under a total pressure of about 500 kg/cm$^2$ to obtain stable emulsions of the invention. The operating temperature is kept in a range of up to about 55° C., and preferably about 25° C. to about 40° C.

The emulsion has a dispersed phase of ultrafine particles with a diameter of less than 0.2 $\mu$m or at most less than 0.3 $\mu$m. Moreover, it is stable, that is, showing no growth in particle size even when heated or stored frozen for a long period of time. Therefore, the emulsion minimizes the risk to a host of any undue and potentially harmful effects resulting from the agglomeration or coalescing of emulsion particles.

The fluorocarbon emulsion may be used as an infusion fluid after being made isotonic to the body fluids of the intended host. Thus, in human, the emulsion can be suspended with commercial plasma extenders such as dextran solution, hydroxyethylstarch and modified gelatin or with physiologic buffers such as salines.

The isotonic emulsions, when oxygenated or not, can serve as a blood substitute, a reperfusion fluid or as a perfusion fluid for preservation of organs to be transplanted, among other uses. In such circumstances, the isotonic fluorocarbon emulsion is administered as any other body fluid, generally intravenously. In the case of perfusing an organ to be transplanted, the organ can be placed into a bath of isotonic oxygenated fluorocarbon emulsion or the major vessels that supply blood to the organ can serve as conduits for the flow of the isotonic oxygenated fluorocarbon emulsion through the organ. The techniques employable are known in the art.

Generally, the fluorocarbon emulsions are stored sterile in the frozen state, for example at temperatures between about −5° C. to about −30° C. The emulsion is thawed immediately before use, generally at 37° C., and rendered isotonic, for example by the addition of suitable buffer solutions, such as sodium bicarbonate, including various metal salts such as potassium chloride, magnesium chloride and calcium chloride, and a small amount of sugar, such as dextrose.

It is widely held in the art that upon thawing the fluorocarbon emulsion, said emulsion must be used within eight hours of thawing. Otherwise, it is believed that the particles begin to agglomerate thereby reducing the beneficial characteristics of the emulsion. Thus, it is a general practice that if the emulsion is not used within eight hours of thawing, the emulsion is discarded.

After mixing, the isotonic emulsion is optionally oxygenated and administered to the host. Once the emulsion is rendered isotonic by the addition of various salts and buffers, the isotonic emulsion generally is used within 24 hours, otherwise the isotonic emulsion is discarded.

The instant invention relates to a method for preparing the isotonic emulsion for administration to hosts in need of treatment or organs in need of perfusion therapy and the like.

Emulsions can be thawed rapidly at temperatures ranging from about 40° C. to about 100° C., say above 40° C. to about up to 96° C., preferably up to about 70° C., more preferably between about 50° C. to about 70° C. After thawing, the emulsion can be held at refrigeration temperatures of about 0° to 15° C., preferably about 2° C. to about 8° C. for several days depending upon the thaw temperature. The optimal temperature of thaw is interrelated with the desired storage temperature after thawing and the length of storage at that temperature after thawing.

Suitable parameters for determining whether an emulsion held for a period of time under controlled temperature conditions retains the desirable physical, chemical and biologic properties include monitoring mean particle diameter, particle diameter distribution, large particle analysis, osmolarity, the concentration of free fluoride ion, partial pressure of oxygen, oxygen content, pH and acute toxicity. Each of those parameters is assessed following the various experimental conditions in determining the method of the instant invention. Of those parameters, mean particle diameter may be the most sensitive to early changes in the suitability of the emulsion.

The mean particle diameter and particle diameter distribution can be measured by inelastic laser light scattering with, for example, a Brookhaven BI-90 Particle Size Analyzer. Commonly, a mean measurement of at least three independent samples is determined.

The osmolarity of the fluorocarbon emulsion can be measured with, for example, an Advanced Instruments Osmometer. The osmometer is calibrated daily with appropriate standards.

The free fluoride ion content of the neat fluorocarbon emulsion can be measured with, for example, an Orion ® fluoride ion electrode.

The number of large particles in the fluorocarbon emulsion can be measured by darkfield phase contrast microscopy. Multiple microscopic fields per sample are photographed and the photographs analyzed to classify and enumerate all particles larger than 1.26 $\mu$m.

The partial pressure of oxygen and the pH of the fluorocarbon before and after oxygenation can be measured with, for example, a Corning Model 158 Blood Gas Analyzer. The analyzer is calibrated with appropriate control solutions at the beginning of each test day.

The oxygen content of the fluorocarbon before and after oxygenation can be measured using various methods and devices available in the art, for example, Lex-$O_2$-Con apparatus was operated as directed by the manufacturer and calibrated with room air as the standard, assuming 20.87% oxygen in dry air at STP. The daily calibration is corrected for temperature, barometric pressure and relative humidity.

The acute toxicity test can be performed by intravenously administering the unoxygenated isotonic samples to rats at a dose of about 50 mL/kg body weight, followed by a seven day observation period. Animals can be considered to have passed the test if they survive seven days with weight gain and without symptoms. Animals that die are necropsied to determine the cause of death.

To determine the range of conditions under which a fluorocarbon emulsion can be thawed without a significant loss of the desirable characteristics thereof, a systematic analysis of differing thaw temperatures was conducted with an assessment of adverse affects based on the various physical, chemical and biologic parameters noted above.

A fluorocarbon emulsion (Fluosol ®, a trademarked product of the Green Cross Corporation, Osaka, Japan) was thawed by placing the frozen bags in either a water bath preheated to 40° C., 50° C., 60° C., 70° C., 84–89° C. or 96–99° C., or by thawing in a refrigerator at 8° C.

The Fluosol ® emulsion has the following composition:

|  | 9/100 ml |
|---|---|
| Perfluorodecalin | 17.5 |
| Perfluorotri-n-propylamine | 7.5 |
| Potoxamer 188* | 3.4 |
| Glycerin, USP | 1.0 |
| Egg yolk phospholipids** | 0.5 |
| Potassium oleate | 0.04 |
| Water for injection, USP | qs |

*$HO-(CH_2CH_2O)_a-[CH(CH_3)(H_2O)]_b-(CH_2CH_2O)_c-H$ where the values for a, b and c are approximately 74, 31 and 74, respectively, and the weight average molecular weight (by gel permeation chromatography) is approximately 8350.
**A mixture of natually occurring phospholipids isolated from egg yolk, having the following general formula:

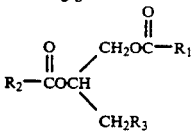

where $R_1$ and $R_2$ are the same saturated and unsaturated fatty acid residues that abound in neutral fats and $R_3$ is primarily either the choline ester or ethanolamine ester function of phosphoric acid.

The bags were not disturbed during the thaw period. Thawing time was defined as the time required for the ice in the bag to melt completely. All bags thawed in water baths were allowed to stand in the bath for about 30 minutes, regardless of the time necessary for complete thawing.

At the end of the thawing period, samples of the fluorocarbon emulsion were taken for determination of mean particle diameter, particle diameter distribution, osmolarity, free fluoride ion and large particle analysis as described herein above. Solutions 1 (30 ml) and 2 (70 ml), which comprise various salts and sugars to render the emulsion isotonic as set forth below, were added to the samples of fluorocarbon emulsion in the correct proportions and then the partial pressure of oxygen, oxygen content, pH and acute toxicity were determined. The prepared fluorocarbon samples were then oxygenated by the bubbling method using the continuous oxygenation kit provided with Fluosol ® for percutaneous transluminal coronary angioplasty by Alpha Therapeutic Corporation of Los Angeles, Calif. and the partial pressure of oxygen, oxygen content and pH again were determined.

| Solution 1 | g/30 ml |
|---|---|
| Sodium bicarbonate, USP | 1.05 |
| Potassium chloride, USP | 0.168 |
| Water for injection, USP | qs |
| Solution 2 | g/70 ml |
| Sodium chloride, USP | 3.004 |
| Dextrose, USP, anhydrous | 0.901 |
| Magnesium chloride . $6H_2O$, USP | 0.214 |
| Calcium chloride . $2H_2O$, USP | 0.178 |
| Water for injection, USP | qs |

The remaining thawed fluorocarbon bags were stored unentered in a refrigerator at 8° C. Bags were selected randomly at predetermined intervals for sampling of the fluorocarbon emulsion. Samples were analyzed for mean particle diameter, particle diameter distribution, osmolarity, free fluoride ion and large particle analysis. Solutions 1 and 2 were added to the samples of fluorocarbon emulsion in the correct proportions and the partial pressure of oxygen, oxygen content, pH and acute toxicity were determined. The prepared fluorocarbon samples then were oxygenated by the bubbling method and the partial pressure of oxygen, oxygen content and pH again were determined.

The thawed fluorocarbon emulsions are stable at 2° to 8° C. for up to 15 days, and for at least eight days of storage at 8° C. after thawing at any temperature up to 70° C., and for at least three days storage at 8° C. after thawing at temperatures in excess of 70° C. and up to 96° C.

The invention will now be described in further detail by way of the following non-limiting examples.

EXAMPLE 1

Fluosol ® is a fluorocarbon stable emulsion in water for injection for oxygen transport. The perfluorochemical phase of the emulsion dissolves oxygen and carbon dioxide. The formulation is a sterile and nonpyrogenic fluid that can be used, for example, for intracoronary administration, percutaneous transluminal coronary angioplasty intravenous administration with or without a fibrinolytic agent to treat and prevent reperfusion injury, ex. when a myocardial infarction has occurred, or as a blood substitute.

Fluosol ® consists of three separate parts which must be mixed prior to use. The first part comprises the actual perfluorochemical emulsion. Fluosol ® is provided in 400 ml aliquots in 500 ml plastic bags. The second part is a solution, called Solution 1, which comprises salts which serve to adjust pH and ionic strength. The third part, termed Solution 2, comprises additional salts and sugar which serve to adjust osmotic pressure in the final 20% emulsion. Solution 1 and Solution 2 are added separately and sequentially prior to administration. These three parts are described hereinbefore.

EXAMPLE 2

The following materials were used in the studies described in the following Examples.

| | |
|---|---|
| Fluorocarbon Emulsion Lot No.: | S0096GR |
| Date of Manufacture: | September 10, 1987 |
| Date Placed on Study: | September, 1990 |
| Shelf Life Status at Study Initiation: | 36 months old or at 150% of the 24 month dating period |
| Fluorocarbon Emulsion Lot No.: | S0104GG |
| Date of Manufacture: | March 30, 1988 |
| Date Placed on Study: | September, 1990 |
| Shelf Life Status at Study Initiation: | 30 months old or at 125% of the 24 month dating period |
| Fluorocarbon Emulsion Lot No.: | S0109GG |
| Date of Manufacture: | August, 1988 |
| Date Placed on Study: | June, 1990 |
| Shelf Life Status at Study Initiation: | 22 months old or at 92% of the 24 month dating period |
| Fluorocarbon Emulsion Lot No.: | S0114HS |
| Date of Manufacture: | March, 1990 |
| Date Placed on Study: | July, 1990 |
| Shelf Life Status at Study Initiation: | 5 months old or at 21% of the 24 month dating period |
| Fluorocarbon Emulsion Lot No.: | S0115HS |
| Date of Manufacture: | March, 1990 |
| Date Placed on Study: | September, 1990 |
| Shelf Life Status at Study Initiation: | 7 months old or at 29% of the 24 month dating period |

All lots of fluorocarbon emulsion used in the study were stored at $-5°$ to $-30°$ C. prior to study.

Solution 1 (lot number C0057HS) and Solution 2 (lot number H0082GU) were used with all fluorocarbon emulsion lots in the study.

EXAMPLE 3

Fluorocarbon bags from lots S0104GG and S0114HS were thawed in a refrigerator at 8° C. Fluorocarbon bags from lots S0109GG and S0114HS were thawed in water baths at 40° C., 50° C. or 60° C. Fluorocarbon bags from lots S0109GG and S0115HS were thawed in water baths at 70° C. Fluorocarbon bags from lots S0096GR and S0115HS were thawed in water baths at one of the maximum bath temperatures of 84–89° C. or 96–99° C.

The time required for thaw of fluorocarbon emulsion placed in an 8° C. refrigerator was 48 hours and thaw times for fluorocarbon placed in water baths varied. Thaw times for the bags were about 25 minutes in a 40° C. bath, about 11 minutes in a 70° C. bath and about 7 minutes in a 96° C. bath.

Test results for mean particle diameter, particle diameter distribution, osmolarity and free fluoride ion concentration showed no difference in the properties for any of the groups of emulsion thawed at 8° C., 40° C., 50° C., 60° C., 70° C., 84° C. or 96° C. for 30 minutes. In addition, all emulsion lots met the mean particle diameter specification of <270 nm with 90% of particles being <400 nm in diameter at all thaw temperatures.

Large particle analysis of the thawed emulsion was determined by darkfield phase contrast microscopy. Results showed no difference in either the total number of large particles or in the distribution of particle diameters in any of the groups of emulsion thawed at any temperature.

There were no differences in oxygen content, pH or acute toxicity. The partial pressure of oxygen after oxygenation appeared to decrease with increasing thaw temperatures; however, the $pO_2$ of the oxygenated fluorocarbon emulsion always exceeded the acceptable oxygenation level of >600 mmHg.

EXAMPLE 4

Fluorocarbon bags from lots S0104GG and S0114HS were thawed in the 8° C. refrigerator. The samples then were stored unopened in a refrigerator at 8° C. Bags were selected randomly at various intervals for determination of mean particle diameter, particle diameter distribution, osmolarity, free fluoride ion, large particle analysis, partial pressure of oxygen, oxygen content, pH and acute toxicity.

There was no difference in the osmolarity or free fluoride ion for any of the groups of emulsion thawed at 8° C. and stored at 8° C. for up to 18 days. The partial pressure of oxygen, oxygen content and pH before and after oxygenation and acute toxicity of the fluorocarbon emulsion also showed no changes upon storage at 8° C.

Large particle analysis showed a slight increase in the total number of particles with diameters greater than 1.26 $\mu$m. This was due to a slight increase in the number of particles with diameters less than 1.88 $\mu$m and reflected the fact that the emulsion particle diameter increase was in its early stages.

EXAMPLE 5

Mean particle diameter was found to be the stability parameter which first exceeded specification and therefore was considered the limiting factor in storage time once thawed.

The mean particle diameter of lot S0104GG samples stored at 8° C. increased from the baseline value of 253 nm at thaw to values which exceeded the specification of <270 nm. The increase was noted first at 15 days.

The mean particle diameter of lot S0114HS samples stored at 8° C. increased from the baseline value of 234 nm at thaw to values greater than 270 nm. The increase was noted first at 18 days.

The mean particle diameter and particle diameter distribution of the 40° C. thawed sample at zero time was used as the baseline value for samples from lot S0114HS. (Assuming an error of ±3° C. in water bath temperature, samples thawed at 40° C. (37–43° C.) were thawed at the temperature now recommended in the Fluosol ® package insert.)

At least 90% of the particles remained below 400 nm at all times during the study, although the value also increased with time.

However, the data showed that the unopened fluorocarbon emulsion was stable when thawed at 8° C. followed by at least 15 days storage at 8° C.

EXAMPLE 6

Fluorocarbon bags from lots S0109GG and S0114HS were thawed at 40° C. and then stored unopened in a refrigerator at 8° C. Bags were selected randomly at various intervals for testing as described in Example 4.

Results of stability testing showed that there was no difference in the osmolarity or free fluoride ion for any of the groups of emulsion thawed at 40° C. and stored at 8° C. for up to 18 days. The partial pressure of oxygen, oxygen content, pH before and after oxygenation and acute toxicity of the fluorocarbon emulsion also showed no changes upon storage at 8° C.

The mean particle diameter of the samples increased upon storage at 8° C. from the initial values at thaw of 250 nm (S0109GG) and 234 nm (S0114HS) to values greater than 270 nm. The increase was noted first at 15 days storage. At least 90% of the particles remained below 400 nm at all times during the study, although the percentage decreased with time. Large particle analysis showed fluctuations without a discernable increase in the number of particles with diameters greater than 1.26 μm.

EXAMPLE 7

Fluorocarbon bags from lots S0109GG and S0114HS were thawed at 50° C. and then stored unopened in a refrigerator at 8° C. Bags were selected randomly at various intervals for testing as described in Example 4.

Results of stability testing showed that there was no difference in the osmolarity or free fluoride ion for any of the groups of emulsion thawed at 50° C. and stored at 8° C. for up to 18 days. The partial pressure of oxygen, oxygen content, pH before and after oxygenation and acute toxicity of the fluorocarbon emulsion also showed no changes upon storage at 8° C.

The mean particle diameter of samples stored at 8° C. increased from the initial value of 247 nm (S0109GG) and the baseline value of 234 nm (S0114HS) at thaw to values greater than 270 nm. The increase was noted first at 11 days storage. The mean particle diameter and particle diameter distribution of the 40° C. thawed sample at zero time was used as the baseline value for the samples of lot S0114HS. At least 90% of the particles remained below 400 nm at all times during the study, although the percentage decreased with time. Large particle analysis showed fluctuations without a discernable increase in the number of particles having diameters greater than 1.26 μm.

EXAMPLE 8

Fluorocarbon bags from lots S0109GG and S0114HS were thawed at 60° C. and then stored unopened in a refrigerator at 8° C. Bags were selected randomly at various intervals for testing as described in Example 4.

Stability test results showed that there was no difference in the osmolarity or free fluoride ion for any of the groups of emulsion thawed at 60° C. and stored at 8° C. for up to 18 days. The partial pressure of oxygen, oxygen content, pH before and after oxygenation and acute toxicity of the fluorocarbon emulsion also showed no change upon storage at 8° C.

The mean particle diameter of samples stored at 8° C. increased from the initial value of 246 nm (S0109GG) and the baseline value of 234 nm (S0114HS) at thaw to values greater than 270 nm. The increase was noted first at 11 days storage. The mean particle diameter and particle diameter distribution of the 40° C. thawed sample at zero time was used as the baseline value for the samples of lot S0114HS. At least 90% of the particles remained below 400 nm at all times during the study, although the percentage decreased with time. Large particle analysis showed fluctuations without a discernable increase in the number of particles with diameters greater than 1.26 μm.

EXAMPLE 9

Fluorocarbon bags from lots S0109GG and S0115HS were thawed at 70° C. and stored unopened in a refrigerator at 8° C. Bags were selected randomly at various intervals for testing as described in Example 4.

Stability test results showed that there was no difference in the osmolarity or free fluoride ion for any of the groups of emulsion thawed at 70° C. and stored at 8° C. for up to 18 days. The partial pressure of oxygen, oxygen content, pH before and after oxygenation and acute toxicity of the fluorocarbon emulsion also showed no changes upon storage at 8° C.

The mean particle diameter of the samples stored at 8° C. increased from the initial values of 251 nm (SO109GG) and 243 nm (S0115HS) at thaw to values greater than 270 nm. The increase was noted first at 15 (S0115HS) to 18 (S0109GG) days. At least 90% of the particles remained below 400 nm at all times during the study, although the percentage decreased with time. Large particle analysis showed fluctuations with no discernable increase in the number of particles having diameters greater than 1.26 μm.

EXAMPLE 10

Too wide of a sampling interval was used for initial testing of the lot S0096GR group. Therefore, when test results for particle diameter were found to be out of specification, it was necessary to test additional bags from the lot to determine at what time point the specification was exceeded.

Additional samples of lot S0096GR were thawed at 73° C. and held from 4 to 8 days at 8° C. Samples were taken daily for measurement of mean particle diameter and particle diameter distribution only. The mean particle diameter was less than 270 nm and 90% of the particles were less than 400 nm for the 8 days of the study.

EXAMPLE 11

Fluorocarbon bags from lots S0096GR and S0115HS were thawed at 84–89° C. and then stored unopened in a refrigerator at 8° C. One bag was selected randomly at various intervals for testing as described in Example 4.

Stability test results showed that there was no difference in the osmolarity or free fluoride ion for any of the bags of emulsion thawed at 84–89° C. and stored at 8° C. for up to 10 or 11 days. The partial pressure of oxygen, oxygen content, pH before and after oxygenation and acute toxicity of the fluorocarbon emulsion also showed no changes upon storage at 8° C.

Additional samples of lot S0096GR (supplemental group) were thawed at 84–89° C. and stored at 8° C. for periods of time. Random samples were taken on a daily basis for determination of mean particle diameter and particle diameter distribution only.

The mean particle diameter of the samples stored at 8° C. increased from the initial value of 240 nm (S0096GR) and 234 nm (S0115HS) at thaw to values greater than 270 nm. The increase was noted first at 8 (S0096GR) and 11 (S0115HS) days. At least 90% of the particles remained below 400 nm at all times during the study, although the percentage decreased with time. Large particle analysis showed fluctuations without a discernable increase in the number of particles with diameters greater than 1.26 μm.

EXAMPLE 12

Fluorocarbon bags from lots S0096GR and S0115HS were thawed at 96-99° C. and then stored unopened in a refrigerator at 8° C. Bags were selected randomly at various intervals for testing as described in Example 4.

Stability test results showed that there was no difference in the osmolarity or free fluoride ion for any of the bags of emulsion thawed at 96-99° C. and stored at 8° C. for up to 10-11 days. The partial pressure of oxygen, oxygen content, pH before and after oxygenation and acute toxicity of the fluorocarbon emulsion also showed no changes upon storage at 8° C.

The mean particle diameter of samples stored at 8° C. increased from the initial value of 251 nm (S0096GR) and 243 nm (S0115HS) at thaw to values greater than 270 nm. The increase was noted first at 8 (S0096GR) and 11 (S0115HS) days. At least 90% of the particles remained below 400 nm at all times during the study, although the percentage decreased with time. Large particle analysis showed fluctuations without a discernable increase in the number of particles with diameters greater than 1.26 $\mu$m.

EXAMPLE 13

A stability indicating parameter is the mean particle diameter. Mean particle diameter increased from the initial or baseline value at thaw to values which exceeded the specification for the product after storage times at 8° C. varying from 3 to 18 days. Mean particle diameter increased rapidly within 4 days, irrespective of the thawing temperature. The mean particle diameter then underwent a slow increase with individual measurement values exceeding the specification for mean particle diameter first appearing after 3 to 18 days of storage at 8° C. Table 1 summarizes the time of storage at 8° C. during which the fluorocarbon emulsion was within specification and maintained a mean particle diameter of less than or equal to 270 nm.

TABLE 1

Time after thawing at specified temperature for 30 minutes followed by storage at 8° C. during which mean particle size was $\leq$270 nm.

| Thaw Temperature °C. | Fluorocarbon Emulsion Lot Number | Time Mean Particle is $\leq$270 nm (days) |
|---|---|---|
| 8° C. | S0104GG | 10 |
|  | S0114HS | 18 |
| 40° C. | S0109GG | 11 |
|  | S0114HS | 18 |
| 50° C. | S0109GG | 11 |
|  | S0114HS | 15 |
| 60° C. | S0109GG | 8 |
|  | S0114HS | 15 |
|  | S0096GR | 8 |
| 70° C. | S0109GG | 11 |
|  | S0115HS | 15 |
| 84° C. | S0096GR | 7 |
|  | S0115HS | 8 |
| 96° C. | S0096GR | 3 |
|  | S0115HS | 8 |

All other measured parameters in the study were essentially unchanged or showed patterns of random fluctuation over the course of the study. The results of the study permit the establishment of stability limits for fluorocarbon based upon the mean particle diameter results.

The mechanism for the increase in mean particle diameter and particle diameter distribution is called "ripening" of the emulsion. It is believed to arise from fusion of two or more smaller particles into a larger particle. Each fusion of two particles of equal size will yield a particle with a diameter 1.26 times that of the parent particles. Thus, a single fusion step of all particles would lead to an increase in the mean particle diameter from an emulsion with a monodisperse diameter of 250 nm to a diameter of 313 nm. For example, the increase observed from 250 nm at the initial thaw to 270 nm for fluorocarbon emulsion lot S0109GG was 1.08 times, which would reflect a fusion of approximately 30% of the particles, in a very simplistic analysis.

The difference between the initial mean particle diameter measurements for lots S0096GR, S0104GG, and S0109GG compared to S0114HS and S0115HS reflected the different points in shelf life at the start of the study. Lot S0096GR had been stored at $-5°$ C. to $-30°$ C. for at least 3 years, lot S0104GG had been stored at $-5°$ C. to $-30°$ C. for at least 2.5 years, lot S0109GG had been stored at $-5°$ C. to $-30°$ C. for at least 1.8 years, while lots S0114HS and S0115HS were stored for less than 5 to 7 months, respectively. However, within 4 days of storage at 8° C., all lots showed similar mean particle diameter in spite of the different initial values.

Although the invention has been described in detail and with reference to specific embodiments thereof, it would be apparent to one skilled in the art that various changes and modification can be made therein without departing from the spirit and scope thereof.

What is claimed is:

1. A process for final preparation prior to administration to a patient of a frozen oxygen transporting fluorocarbon emulsion, without degrading pharmacologic properties thereof, comprising rapidly thawing a frozen oxygen transporting fluorocarbon emulsion at a temperature above 40° C. and thereafter storing said thawed emulsion in a liquid state for from over eight hours up to 15 days prior to its administration.

2. The process of claim 1, wherein said frozen emulsion is thawed at above about 40° C. to about 100° C.

3. The process of claim 2, wherein said frozen emulsion is thawed up to about 70° C.

4. The process of claim 3, wherein said frozen emulsion is thawed at about 50° C. to about 70° C.

5. The process of claim 2, wherein said emulsion is stored thawed at a temperature of about 0° to 15° C. for over eight hours.

6. The process of claim 4, wherein said emulsion is stored thawed at a temperature of about 0° to 15° C. for over eight hours.

7. The process of claim 2, wherein said emulsion is stored thawed at a temperature of about 2° to 8° C. for 1 to 15 days.

8. The process of claim 4, wherein said emulsion is stored thawed at a temperature of about 2° to 8° C. for 1 to 15 days.

* * * * *